United States Patent
Yamagishi

(10) Patent No.: US 7,955,076 B2
(45) Date of Patent: Jun. 7, 2011

(54) CARIOUS TOOTH DETECTION DEVICE

(75) Inventor: Atsushi Yamagishi, Tokyo (JP)

(73) Assignee: Kao Corporation, Tokyo (JP)

( * ) Notice: Subject to any disclaimer, the term of this patent is extended or adjusted under 35 U.S.C. 154(b) by 575 days.

(21) Appl. No.: 10/551,842

(22) PCT Filed: Apr. 2, 2004

(86) PCT No.: PCT/JP2004/004861
§ 371 (c)(1),
(2), (4) Date: Nov. 15, 2005

(87) PCT Pub. No.: WO2004/089197
PCT Pub. Date: Oct. 21, 2004

(65) Prior Publication Data
US 2007/0105069 A1    May 10, 2007

(30) Foreign Application Priority Data
Apr. 3, 2003   (JP) ................ 2003-099917

(51) Int. Cl.
*A61C 3/00*   (2006.01)
(52) U.S. Cl. .................................... 433/29
(58) Field of Classification Search .......... 433/29, 433/215; 600/407, 473, 475–477; 250/461.1, 250/461.2, 458.1, 459.1
See application file for complete search history.

(56) References Cited

U.S. PATENT DOCUMENTS

| | | | | |
|---|---|---|---|---|
| 4,479,499 A | * | 10/1984 | Alfano | 433/29 |
| 5,382,163 A | * | 1/1995 | Putnam | 433/215 |
| 6,522,407 B2 | * | 2/2003 | Everett et al. | 356/369 |
| 2002/0093655 A1 | * | 7/2002 | Everett et al. | 356/369 |
| 2003/0156788 A1 | * | 8/2003 | Henning | 385/31 |
| 2005/0181333 A1 | * | 8/2005 | Karazivan et al. | 433/29 |

FOREIGN PATENT DOCUMENTS

| | | |
|---|---|---|
| EP | 0 555 645 | 8/1993 |
| JP | 56-40137 | 4/1981 |
| JP | 10-216085 | 8/1998 |
| JP | 2000-23903 | 1/2000 |
| JP | 2001-24223 | 1/2001 |
| JP | 2001-299699 | 10/2001 |
| WO | WO 03/005892 A2 | 1/2003 |

OTHER PUBLICATIONS

Stookey et al. "Dental Caries Diagnosis", Cariology, vol. 43, No. 4, pp. 665-677 1999.
Shi et al. "Comparison of QLF and DIAGNOdent for Quantification of Smooth Surface Caries", Caries Research, vol. 35, pp. 21-26 2001.
Yoshikawa et al. "The Influence of pH and Exposure Time of 0.1M Lactic Acid on Demineralization of Enamel", Journal of Dental Health, vol. 40, pp. 671-677, with English abstract 1990.

* cited by examiner

*Primary Examiner* — Cris L Rodriguez
*Assistant Examiner* — Heidi M Eide
(74) *Attorney, Agent, or Firm* — Oblon, Spivak, McClelland, Maier & Neustadt, L.L.P.

(57) ABSTRACT

A dental caries detecting system 1 according to the invention includes an ultraviolet irradiation device 2, a fluorescence receiving device 3 that receives fluorescence from a tooth based on ultraviolet irradiation from the ultraviolet irradiation device 2, a fluorescence data analysis portion 4 that analyzes fluorescence data transmitted from the fluorescence receiving device 3, and a display 5 that displays analysis data analyzed by the fluorescence data analysis portion 4. The fluorescence data analysis portion 4 is adapted to analyze said fluorescence data based on the fluorescence intensities in at least two wavelength bands in a visible light range.

20 Claims, 10 Drawing Sheets

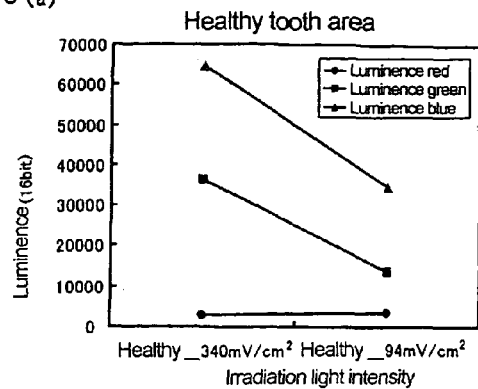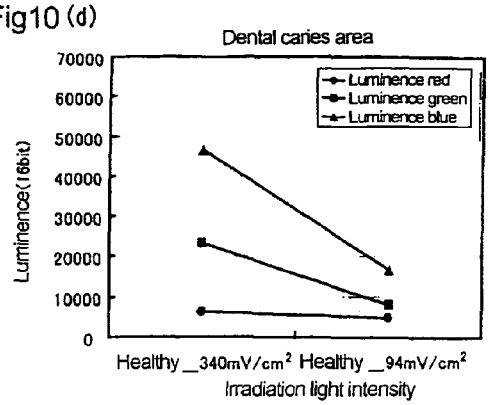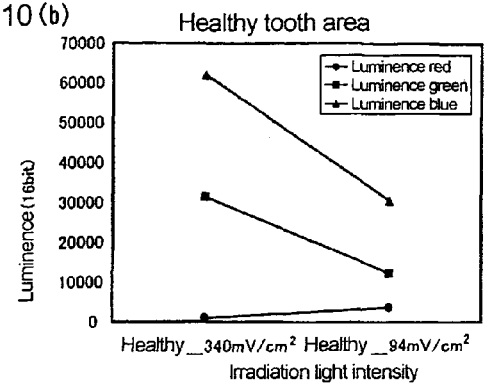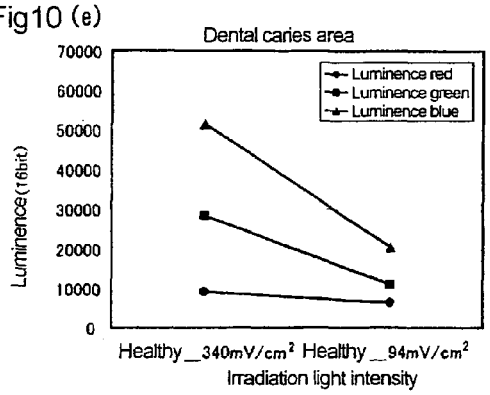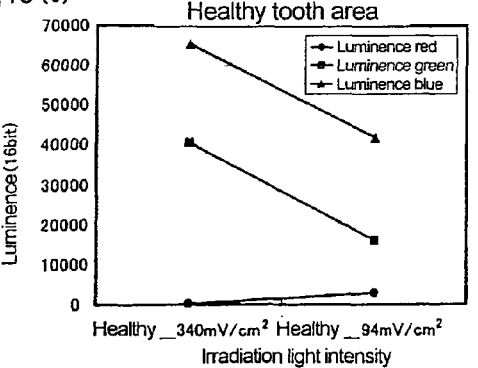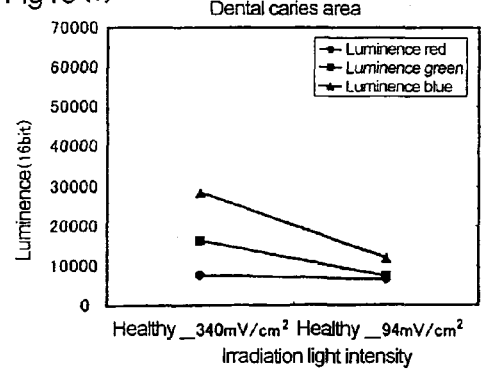

CARIOUS TOOTH DETECTION DEVICE

TECHNICAL FIELD

The present invention relates to a technique of detecting dental caries, and more particularly, to a technique of non-destructively detecting dental caries in early stages based on fluorescence information from teeth.

BACKGROUND ART

Technical Document 1 (Japanese Patent Laid-Open Publication No. 2001-299699) discloses a conventional technique of detecting dental caries using light. The disclosed device irradiates a tooth with red light (600 nm to 670 nm) as excitation light and measures only the intensity of fluorescence from the tooth received by a photodiode. The device detects dental caries using fluorescence emitted from oral bacteria, and therefore dental caries can be detected when it progresses so far as to form a cavity in the tooth, and bacteria proliferation is in progress inside the cavity.

However, the degree of progress of primary dental caries is not strictly related to the presence and number of bacteria. It is often the case with primary dental caries in particular that no such bacteria in an oral composition are detected in affected locations, and therefore it is difficult to detect primary dental caries using the device disclosed by Patent Document 1. More specifically, the analysis result according to the fluorescence information depends on the presence/absence of oral bacteria, and therefore it is difficult to accurately identify the presence/absence of primary dental caries using the device.

In order to solve the disadvantage associated with the device disclosed by the above Technical Document 1, QLF (quantitative light-induced fluorescence) method disclosed by Technical Document 2 (Stookey, G. K., et al., Dental caries diagnosis, Dent Clin North Am., 43; 665-77, 1999) and Technical Document 3 (Shi, X. Q., et al., Comparison of QLF and DIAGNOdent for qualification of smooth surface caries, Caries Res., 35(1): 21-6, 2001) and a device based on the method have been developed. The device irradiates a tooth with an ultraviolet beam of 380±70 nm, and detects only the intensity of fluorescence not less than 520 nm, and the technology takes advantage of the phenomenon that the intensity of fluorescence at a dental caries area is lower than that from a healthy area. The dental caries detection in this case is unaffected by the presence of bacteria, and therefore the presence/absence of dental caries can be detected more accurately than the device disclosed by Technical Document 1. As will be described in connection with the following Comparative Example 2, change in an actual mineral decreasing ratio does not match change in the fluorescence intensity not less than 520 nm, and therefore the degree of progress of primary dental caries cannot be measured in this way.

Technical Document 4 (European Patent Publication No. 0555645, Description) discloses a dental caries detecting device that irradiates a tooth with an ultraviolet beam in the range from 360 nm to 580 nm and measures fluorescence not less than 620 nm from the tooth. The device measures only red fluorescence specific to a dental caries area and does not detect oral bacteria as in Technical Document 1. The device according to Technical Document 4 is however directed to measuring only red fluorescence whose intensity is low, which is not sufficient for detecting the presence/absence of dental caries and is liable to the effect of the measurement environment such as the effect of external light. This lowers the detection sensitivity.

Meanwhile, as a technique of accurately detecting and quantitatively determining the degree of progress of dental caries is disclosed by Technical Document 5 (Tadashi Yoshikawa, et al., "The Effect of pH and Acting Time of 0.1M Lactic Acid Upon Decalcification of Enamel," Journal of Dental Health, Vol. 40, pp. 671 to 677, 1990). According to the disclosed technique, an extracted decayed tooth is sliced and a micro X-ray photograph of its section is taken. The tooth is compared to a healthy tooth based on information in the photograph, and the mineral decreasing ratio is calculated to quantitatively determine the progress of the dental caries. The progress of dental caries can surely be determined by this method, but the tooth must be removed and sliced in order to carry out the measurement.

Therefore, there has been a demand for dental caries detecting device and method that allow to accurately detect primary dental caries with high sensitivity, and allow the degree of progress of dental caries to be also detected.

DISCLOSURE OF THE INVENTION

The inventors have found that when a healthy tooth is irradiated with an ultraviolet beam (i-ray of 365 nm from a mercury lamp), strong fluorescence is generated about in the range from 400 nm to 500 nm (corresponding to blue). While dental caries is irradiated with the same beam, fluorescence about in the range from 400 nm to 500 nm is weak and fluorescence about in the range from 600 nm to 800 nm (corresponding to red) is generated.

The inventors have also found that when the intensity of ultraviolet irradiation is reduced, fluorescence corresponding to blue and red is lowered for dental caries, while for a healthy tooth, the fluorescence corresponding to blue is weaker but fluorescence corresponding to red is stronger.

The invention was made based on the above-described findings. A dental caries detecting device according to the invention includes an ultraviolet light source, a fluorescence receiving portion that receives fluorescence from a tooth based on ultraviolet irradiation from the ultraviolet light source, a fluorescence data analysis portion that analyzes fluorescence data transmitted from the fluorescence receiving portion, and an analysis data display portion that displays analysis data analyzed by the fluorescence data analysis portion. The fluorescence data analysis portion analyzes the fluorescence data based on the fluorescence intensities in at least two wavelength bands in a visible light range.

The use of the detecting device according to the invention allows primary dental caries to be detected with high sensitivity, so that non-surgical treatment of primary dental caries without cutting the affected area can be carried out more easily. The dental caries detecting device according to the invention can measure the degree of progress of dental caries. The process of treatment of the primary dental caries can be observed, and the degree of recovery can be checked. Therefore, the progress of the dental caries or its recovery can specifically be pointed out to the patient. The importance and effects of dental caries prevention treatment can be appreciated, which can contribute to maintenance and improvement of oral health.

The dental caries detecting device according to the invention measures the surface of a tooth, so that dental caries can be detected more precisely, and areas between teeth that are difficult to measure can be measured (measured in one location), or a healthy area and a dental caries area of a tooth can be compared and measured (measured in two locations). The fluorescence data is analyzed based on fluorescence intensities in at least two wavelength bands in the visible light range, so that dental caries (primary dental caries in particular) and its degree of progress can accurately be detected with high sensitivity.

Furthermore, using the dental caries detecting device according to the invention, a wavelength band showing different changes between a dental caries area and a healthy tooth area can be selected in fluorescence data from a tooth that changes according to change in the intensity of ultraviolet irradiation, so that analysis can be carried out based on a plurality of fluorescence intensities in the wavelength band. In this way, the presence of dental caries (primary dental caries in particular) and its progress degree can accurately be detected with high sensitivity.

In this application, the "first wavelength band" shall refer not only to the red-corresponding wavelengths but also to a wavelength band selected from the wavelength band from 550 nm to 810 nm including wavelengths corresponding to green and having an arbitrary wavelength width. The "second wavelength band" shall refer not only to the blue-corresponding wavelengths but also to a wavelength band selected from the wavelength band of 380 nm to 550 nm including the green-corresponding wavelengths and having an arbitrary wavelength width. The "third wavelength band" shall refer not only to the green-corresponding wavelengths, but also to a wavelength band selected from the wavelength band of 450 nm to 650 nm including the red-corresponding wavelengths and the blue-corresponding wavelengths and having an arbitrary wavelength width.

The wavelength width of the first wavelength band is from 0.1 nm to 260 nm, preferably from 10 nm to 260 nm, more preferably from 50 nm to 260 nm. The wavelength width of the second wavelength band is from 0.1 nm to 170 nm, preferably from 10 nm to 170 nm, more preferably from 50 nm to 170 nm. The wavelength width of the third wavelength band is from 0.1 nm to 200 nm, preferably from 10 nm to 200 nm, more preferably from 50 nm to 200 nm.

When fluorescence data is divided into data pieces in a plurality of wavelength bands using a band-pass filter, the numerical range of wavelengths included in each wavelength band can change depending on the characteristic of the filter. For example, using a primary color CCD having a band-pass filter already incorporated, the central wavelength is typically 650±50 for the first wavelength band (corresponding to red), 450±50 for the second wavelength band (corresponding to blue), and 550±50 for the third wavelength band (corresponding to green). However, other than these wavelength ranges, the wavelength bands may overlap one another depending on the characteristic of the filter.

The central wavelengths of the first and the third wavelength bands are preferably at least 10 nm apart, more preferably at least 20 nm apart. The central wavelengths of the second and third wavelength bands are also preferably at least 10 nm apart, more preferably at least 20 nm apart. Note that the central wavelength refers to the intermediate wavelength between two points having a relative transmittance of 50% in a band pass filter.

Using the filter having the filter characteristic in FIG. 1, the red wavelength band is from 350 to 450 and from 550 to 750, which is included in the first wavelength band in this application.

BRIEF DESCRIPTION OF THE DRAWINGS

FIGS. 10A to 10F show the relation between the light intensity and the luminance used in Examples 1 to 4, among which FIG. 10A is a graph showing a healthy tooth area (minor); FIG. 10B is a graph showing a healthy tooth area (moderate); FIG. 10C is a graph showing a healthy tooth area (severe); FIG. 10D is a graph showing a minor dental caries area; FIG. 10E is a graph showing a moderate dental caries area; and FIG. 10F is a graph showing a severe dental caries area.

BEST MODE FOR CARRYING OUT THE INVENTION

Now, a dental caries detecting device, a dental caries detecting method, and a dental caries detecting program according to a preferred embodiment of the invention will be described in connection with the accompanying drawings.

Figure 1:
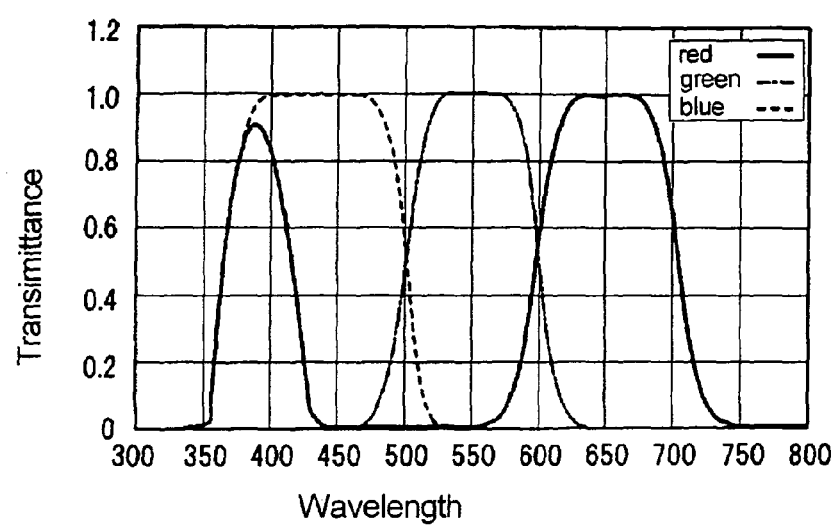
FIG. 1 shows the filter characteristic of a color CCD.
Figure 2:
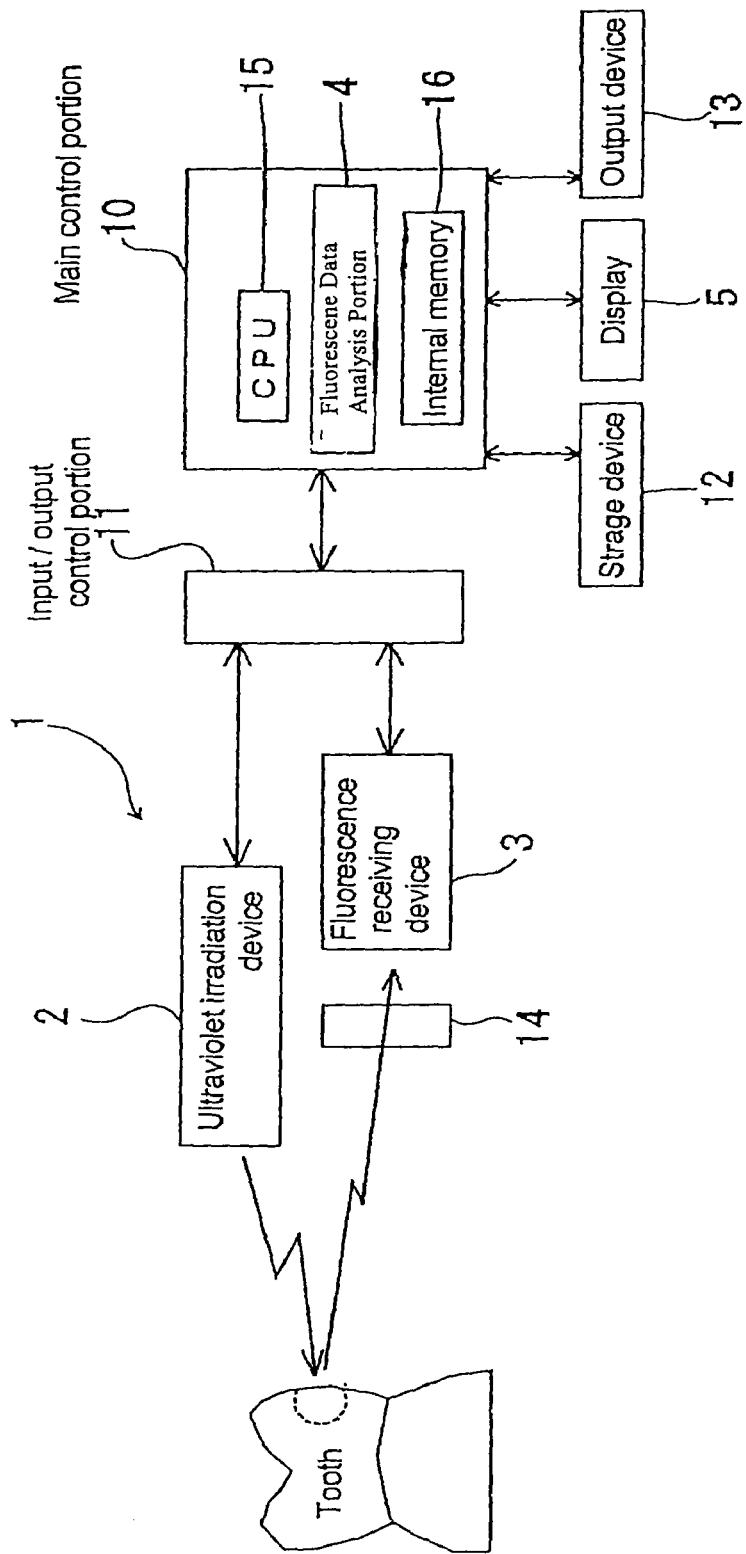
FIG. 2 shows the general structure of a dental caries detecting system according to an embodiment of the invention.

As shown in FIG. 2, a dental caries detecting system (dental caries detecting device) 1 according to the embodiment includes an ultraviolet irradiation device (ultraviolet light source) 2, a fluorescence receiving device (fluorescence receiving portion) 3 that receives fluorescence emitted from a tooth in response to ultraviolet irradiation from the ultraviolet irradiation device 2, a data analysis portion 4 that analyzes data transmitted from the fluorescence receiving device 3, and a display (analysis data display portion) 5 that displays analysis data analyzed by the data analysis portion 4.

The data analysis portion 4 divides fluorescence data into data pieces in two or more wavelength bands in the visible light range, and can analyze the data pieces based on the fluorescence intensities in the respective wavelength bands.

Now, the dental caries detecting system 1 will be described in detail.

The dental caries detecting system 1 has a main control portion 10 (that will be detailed) that controls the system as a whole. The main control portion 10 is connected with the ultraviolet irradiation device 2 and the fluorescence receiving device 3 through an input/output control portion 11 and also connected with a storage device 12, a display 5, and an output device 13.

The ultraviolet irradiation device 2 may be any type that irradiates an ultraviolet beam about in the range from 300 nm to 400 nm, and has an adjustable irradiation intensity. The ultraviolet irradiation device 2 is, for example, an ultraviolet LED, a mercury lamp, and a metal halide lamp. The ultraviolet LED can have its ultraviolet irradiation intensity adjusted. For example, the light intensity may be adjusted as the input/output control portion 11 controls the amount of current passage or adjusted by changing the number of LEDs to be turned on.

In the mercury lamp or metal halide lamp, irradiated light passes through a visible light cut filter and becomes ultraviolet light whose intensity can be adjusted. The intensity can be adjusted, for example, by controlling the current value or using an ND filter.

A material to guide ultraviolet light from the ultraviolet irradiation device 2 is not specified and may be any material having low ultraviolet absorptivity such as an optical fiber having a core made of quartz glass or a polymer material, through which light is directly irradiated upon a tooth.

In the fluorescence receiving device 3, light in the ultraviolet range is absorbed as fluorescence from a tooth caused by the ultraviolet irradiation passes the ultraviolet cut filter 14, and only light in the visible light range is received by the optical device through the optical fiber. The optical device may be any device that can obtain information including color information as fluorescence data from the fluorescence in the visible light range, and can transmit the information to the input/output control portion 11.

The input/output control portion 11 A/D-converts the information from the optical device.

The above-described optical device may be, for example, a spectroscopic luminance meter, a color CCD, a CMOS, or an optical sensor with a color filter for two or more colors.

More specifically, the spectroscopic luminance meter separates fluorescence into color lights (red, green, and blue lights and the like) using a prism or the like, and these color lights are taken into the optical sensor to obtain information about each of the colors.

The color CCD receives light at its two-dimensionally arranged elements having color filters (for RGB primary colors, and CMYG complementary colors) and obtains color information based on electrical signals from these elements.

More specifically, the optical sensor having a color filter for two or more colors (band-pass filter) obtains information only on fluorescence in a particular wavelength for each of wavelength bands based on electrical signals from light receiving elements such as a photo-multiplier and a silicon photodiode.

The storage device may be any device that can store analysis data obtained from the data analysis portion 4 such as a hard disk, a flexible disk, and an optical disk.

The display 5 may be any device that can display the above-described analysis data and information necessary for selecting analysis data (such as the number of measuring areas and change in the light intensity), and, for example, a CRT display or a liquid crystal display can be used.

The output device 13 may be any device that can output the analysis data described above and, for example, a printer can be used.

The main control portion 10 includes a CPU 15, an internal memory 16, and a fluorescence data analysis portion 4. The CPU 15 decodes and carries out instructions from a control program such as an OS (operating system) and a dental caries detecting program. The internal memory 16 temporarily stores information from the input/output control portion 11 or analysis data from the storage device 12.

The fluorescence data analysis portion 4 is implemented as means including the dental caries detecting program, the CPU 15, and a hardware resource (computer) such as a main memory acting in corporation with one another when the dental caries detecting program is carried out by the CPU 15.

The dental caries detecting program can enable the CPU 15 to carry out a measuring area number selecting function, a light intensity changing function, a data obtaining function, a wavelength band selecting function, a dental caries degree operating function, and a dental caries presence/absence and progress degree determining function. The following dental caries detecting method is made of these functions.

Now, the dental caries detecting method according to the embodiment will be described in association with various functions enabled by the dental caries detecting program with reference to FIGS. 3 to 9.

The dental caries detecting methods share the main processing (S1 to S3, S5) and are largely divided into three kinds depending upon the difference in the purpose or method of detection, i.e., a single area measuring method (S4, S11 to S19), a comparison measuring method (S21 to S30), and a light intensity change measuring method (S31 to S35, S41 to S48, S51 to S58, S61 to S68).

According to the single area measuring method, the presence/absence of dental caries or the progress degree of the dental caries is detected at a visually observable caries area, an area suspected to have dental caries, or a dental caries area located, for example, between teeth or an occluded area that is not visually observable. According to the method, a single location suspected to have dental caries is measured at least once.

According to the comparison measuring method, the presence/absence or progress degree of dental caries is detected in a visually observable dental caries area or an area suspected to have dental caries (hereinafter simply as "dental caries area"). According to the method, the same tooth is measured independently in two locations, i.e., locations in a dental caries area and a healthy area.

According to the light intensity change measuring method, the presence/absence and progress degree of dental caries are detected regardless of whether or not a dental caries area is visually observable. According to the method, the light intensity of ultraviolet irradiation is varied, while a location suspected to have dental caries is measured a number of times.

Figure 3:
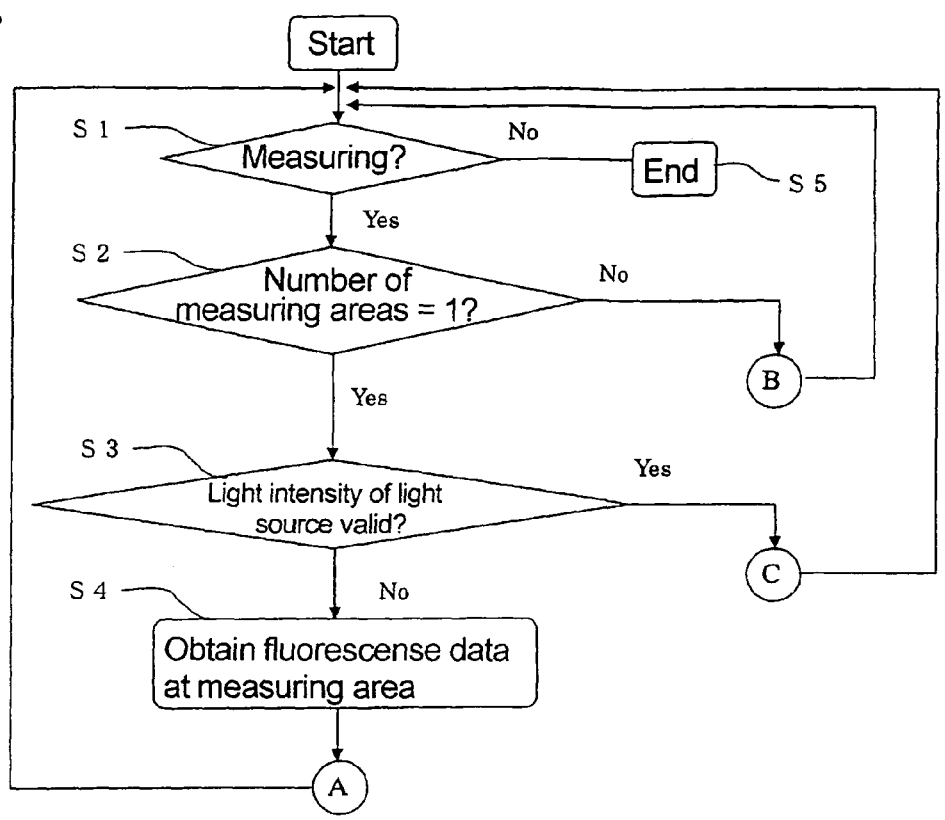
FIG. 3 is a flowchart showing dental caries detecting processing (main processing and single area measuring processing) based on a dental caries detecting program according to the embodiment.

More specifically, as shown in FIG. 3, the CPU 15 controls the display 5 to indicate whether or not to measure (S1), and if the measurement is to be carried out, the CPU controls the display to indicate whether or not the number of measuring areas is "1" (S2).

If the number of measuring areas is not "1," the process branches to processing according to the "comparison measuring method" (branch B that will be detailed), and if the number of measuring areas is "1," the CPU 15 controls the display to indicate whether or not to change the light intensity of the light source depending on the light intensity change selecting function according to the dental caries detecting program (S3).

If the light intensity of the light source is changed, the process branches to the "light intensity change measuring method" (branch C that will be detailed), and if the light intensity of the light source is not changed, the CPU 15 carries out the processing according to the "single area measuring method."

Now, according to the single area measuring method, the operator irradiates an area of interest using the ultraviolet irradiation device 2, and then obtains information from the tooth using the fluorescence receiving device 3.

Then, the CPU 15 obtains the information from the optical device into the internal memory 16 as AD-converted digital signals by the input/output control portion 11 based on the data obtaining function enabled by the dental caries detecting program, and stores luminance values (fluorescence intensities) R, B, and G for each of the first to third wavelength bands in the internal memory 16 (S4).

Herein, the first wavelength band (corresponding to red) preferably has wavelengths from 550 nm to 810 nm in the visible light range (380 nm to 810 nm), more preferably in the range from 600 nm to 700 nm.

The second wavelength band (corresponding to blue) preferably has wavelengths from 380 nm to 550 nm in the visible light range, more preferably from 400 nm to 500 nm.

The third wavelength band (corresponding to green) preferably has wavelengths from 450 nm to 650 nm in the visible light range, more preferably from 500 nm to 600 nm.

Figure 4:
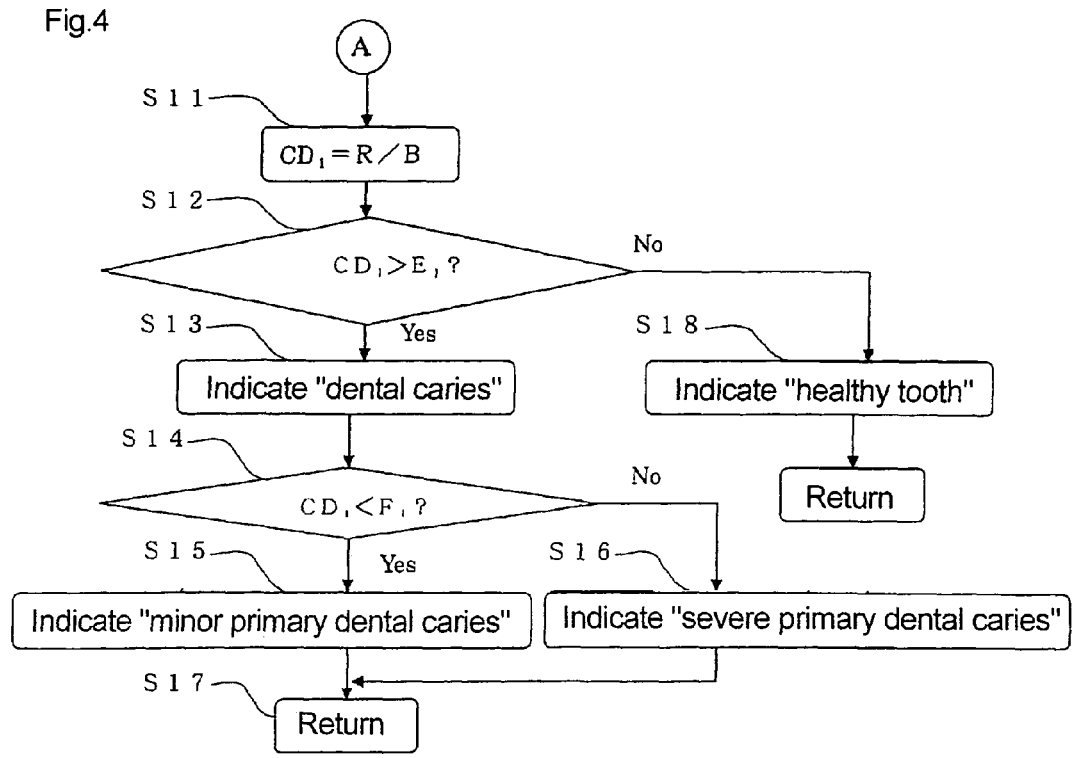
FIG. 4 is a flowchart showing dental caries detecting processing (single area measuring processing, $CD_1$) based on the dental caries detecting program according to the embodiment.

Then, as shown in FIG. 4, the CPU 15 obtains luminance values R, B, and G according to the dental caries degree operating function enabled by the dental caries detecting program, and carries out calculation to obtain a dental caries degree $CD_1$ (S11) based on the values according to the following formula (1):

$$CD_1 = R/B \qquad \text{formula (1)}$$

The dental caries degree $CD_1$ is based on the characteristic that the luminance value R of the dental caries area increases while the luminance values B and G decrease as a dental caries progresses, and the degree of progress of dental caries is represented by a quantitative increasing function.

In this case, the absolute intensity of the luminance B is larger than the luminance G, and therefore external effects such as external light are small and noise is small. Therefore, the dental caries degree $CD_1$ can be calculated with higher precision.

Using the luminance G in place of the luminance B, a dental caries degree $CD_{12}$ can be calculated according to the following formula (1.2):

$$CD_{12} = R/G \qquad \text{formula (1.2)}$$

The processing from steps S12 to S19 is carried out by the CPU 15 according to the dental caries presence/absence and progress degree determining function enabled by the dental caries detecting program.

In step S12, the dental caries degree $CD_1$ is compared to a lower threshold $E_1$. Herein, the "lower threshold" shall refer to a value used for distinguishing a healthy tooth from dental caries (particularly primary dental caries, which also applies to the following description), and the threshold varies depending on conditions such as the irradiation intensity and the irradiation area by the ultraviolet irradiation device 2 or conditions such as the optical path length and the sensitivity of the light receiving elements in the fluorescence receiving device 3. The threshold is determined by calibration in the dental caries detecting system 1.

If the dental caries degree $CD_1$ is equal to or smaller than the lower threshold $E_1$, it is indicated that the tooth is healthy (analysis data), and the process returns to S1 in the main processing (S18 and S19). If the dental caries degree $CD_1$ is larger than the lower threshold $E_1$, it is indicated that there is dental caries (analysis data) (S13).

In S14, the dental caries degree $CD_1$ is compared to an upper threshold $F_1$. Herein, the "upper threshold" shall refer to a value used for distinguishing minor dental caries from severe dental caries, and is determined in the same manner as the lower threshold.

If the dental caries degree $CD_1$ is smaller than the upper threshold $F_1$ it is indicated that there is minor primary dental caries (analysis data) (S15). If the dental caries degree $CD_1$ is equal to or larger than the lower threshold $F_1$, it is indicated that there is severe primary dental caries (analysis data) (S16), and the process returns to S1 in the main processing (S17).

In step S2, if the number of measuring areas is not "1," the CPU 15 carries out the processing according to the "comparison measuring method."

Now, according to the comparison measuring method, the operator irradiates a dental caries area (dental caries suspected area) and a healthy area in the vicinity at the same tooth with ultraviolet light using the ultraviolet irradiation device 2. Then, the operator obtains first information from fluorescence at the dental caries area and second information from fluorescence at the healthy area using the fluorescence receiving device 3.

Figure 5:
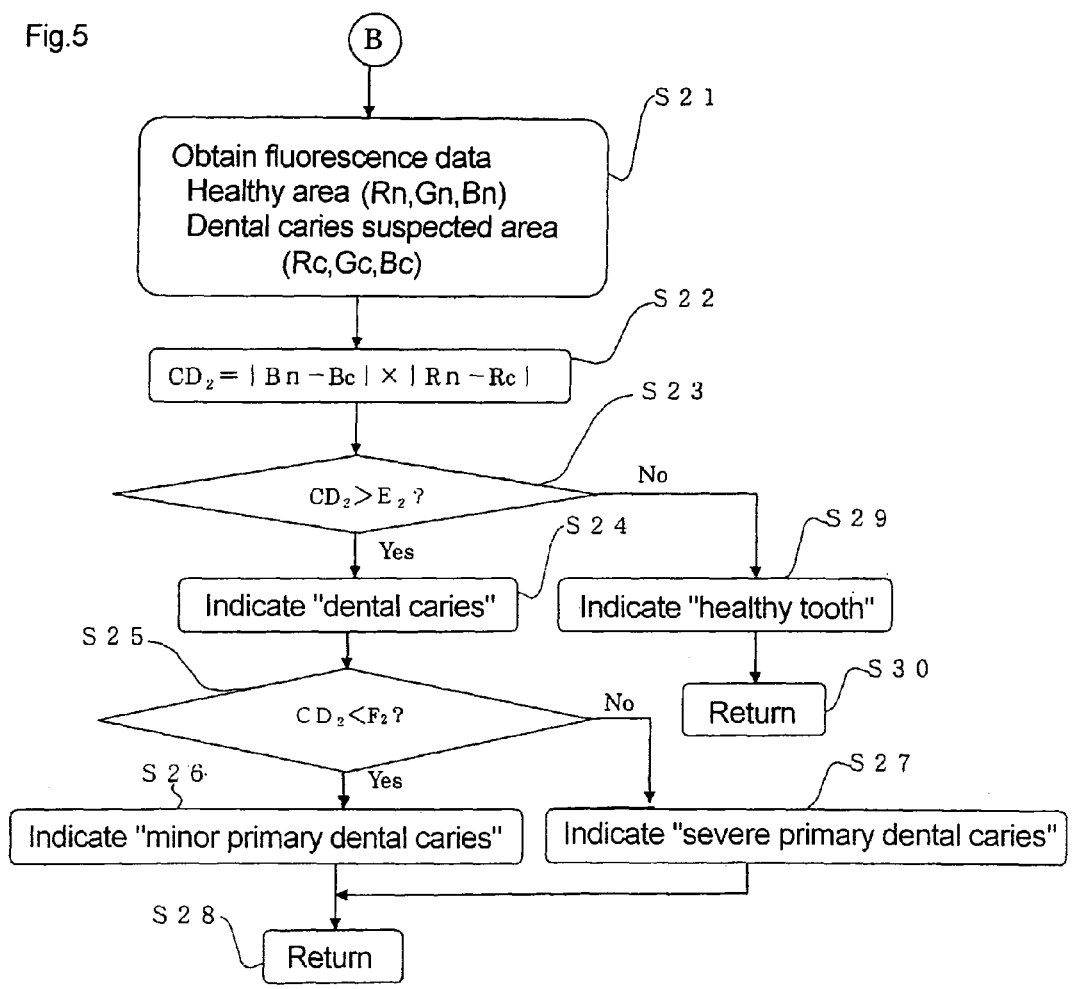
FIG. 5 is a flowchart showing dental caries detecting processing (comparison measuring processing, $CD_2$) based on the dental caries detecting program according to the embodiment.

Now, as shown in FIG. 5, the CPU 15 obtains the first and second information from the optical device as digital signals AD-converted by the input/output control portion 11 according to the data obtaining function enabled by the dental caries detecting program, and the digital signals are stored in the internal memory 16 as the luminance of the dental caries area ($R_c$, $B_c$, $G_c$) of the dental caries area and the luminance ($R_n$, $B_n$, $G_n$) of the healthy area divided for each of the first to third wavelength bands according to the wavelength band selecting function enabled by the dental caries detecting program (S21).

Then, the CPU 15 obtains the average value of each of the luminance values ($R_c$, $B_c$, $O_c$) of the dental caries area and the luminance values of ($R_n$, $B_n$, $G_n$) of the healthy area according to the dental caries degree operating function enabled by the dental caries detecting program, and using the obtained average values, the dental caries degree $CD_2$ is calculated (S22) according to the following formula (2):

$$CD_2 = |R_n - R_c| \times |B_n - B_c| \qquad \text{formula (2)}$$

The dental caries degree $CD_2$ is based on the characteristic that the luminance value $R_c$ of the dental caries area is larger than the luminance value $R_n$ of the healthy area and the luminance values $B_c$ and $G_c$ of dental caries area are smaller than the luminance values $B_n$ and $G_n$ of the healthy area as the dental caries progresses. The degree of progress of dental caries is represented by a quantitative increasing function.

In this case, the absolute intensity of the luminance B is larger than the luminance G, and therefore the effect of external light or the like is less likely and noise is small. Therefore, in view of improving the accuracy of the dental caries degree $CD_1$, the luminance G is not used, but simply in view of comparison to the luminance R, the dental caries degree $CD_{22}$ may be calculated using the luminance G instead of the luminance B according to the following formula (2.2). Alternatively, using the luminance G as well as the luminance B, the dental caries degree $CD_{23}$ may be calculated according to the following formula (2.3):

$$CD_{22} = |R_n - R_c| \times |G_n - G_c| \qquad \text{formula (2.2)}$$

$$CD_{23} = |R_n - R_c| \times \{|B_n - B_c| + |G_n - G_c|\} \qquad \text{formula (2.3)}$$

The processing from S23 to S30 is the processing carried out by the CPU 15 according to the dental caries presence/absence and progress degree determining function enabled by the dental caries detecting program, and substantially the same as the processing from S12 to S19.

In step S23, the dental caries degree $CD_2$ is compared to a lower threshold $E_2$.

If the dental caries degree $CD_2$ is equal to or smaller than the lower threshold $E_2$, it is indicated that the tooth is healthy and the process returns to S1 in the main processing (S29, S30). If the carried degree $CD_2$ is larger than the lower threshold $E_2$, it is indicated that there is dental caries (S24).

In step S25, the dental caries degree $CD_2$ is compared to an upper threshold $F_2$.

If the dental caries degree $CD_2$ is smaller than the upper threshold $F_2$, it is indicated that there is minor primary dental caries (S26). If the dental caries degree $CD_2$ is equal to or larger than the upper threshold $F_2$, it is indicated that there is severe primary dental caries (S27), and the process returns to S1 in the main processing (S28).

In step S3, when the light intensity of the light source is changed, the CPU 15 carries out processing according to the "light intensity change measuring method."

Now, according to the light intensity change measuring method, using the ultraviolet irradiation device 2, the operator irradiates the same area of the same tooth with ultraviolet light having different light intensities $U_1$ and $U_2$ ($U_1 > U_2$). Using the fluorescence receiving device 3, first information is obtained from the fluorescence for the light intensity $U_1$ and second information is obtained from the fluorescence for the light intensity $U_2$.

Figure 6:
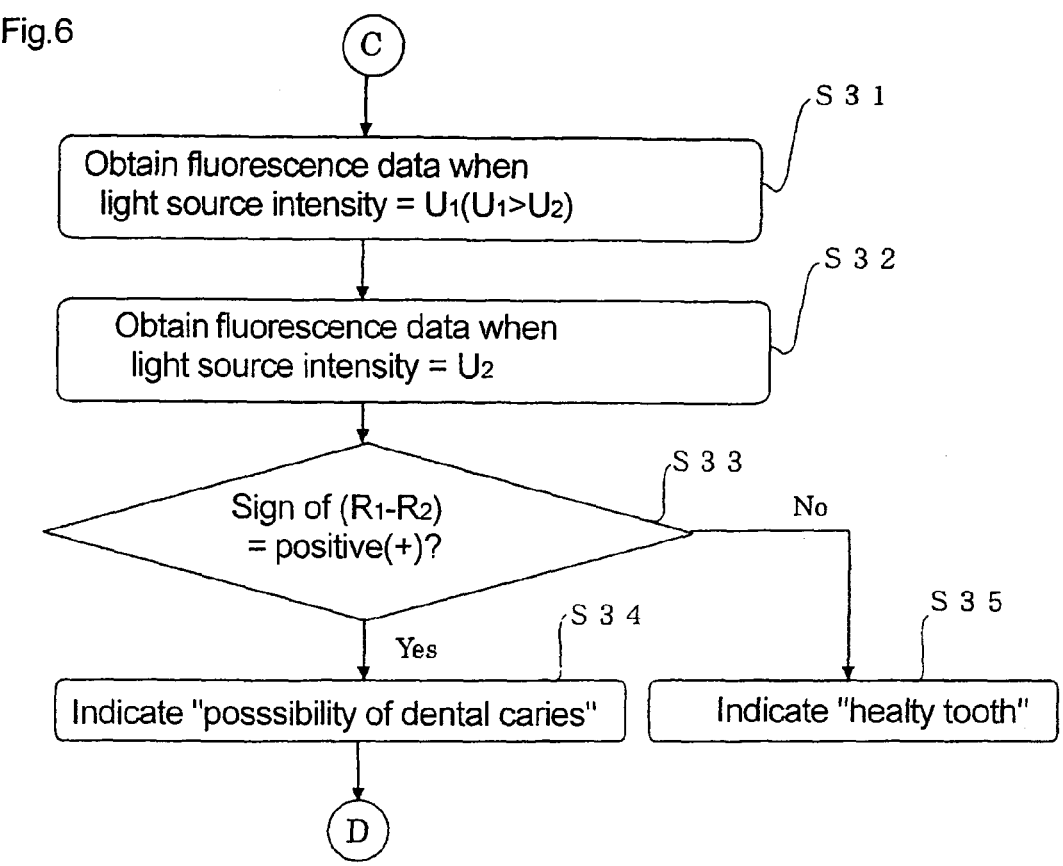
FIG. 6 is a flowchart showing dental caries detecting processing (light intensity change measuring processing) based on the dental caries detecting program according to the embodiment.

Now, as shown in FIG. 6, the CPU 15 obtains the first and second information from the optical device as digital signals AD-converted by the input/output control portion 11 according to the data obtaining function enabled by the dental caries detecting program, and the digital signals are stored in the internal memory 16 as the luminance ($R_1$, $B_1$, $G_1$) for the light intensity $U_1$ and the luminance ($R_2$, $B_2$, $G_2$) for the light intensity $U_2$ for each of the first to third wavelength bands (S31, S32). There may be two or more light intensity values.

Then, the CPU 15 determines the relation between the luminance $R_1$ of the light intensity $U_1$ and the luminance $R_2$ of the light intensity $U_2$ according to the dental caries presence/absence and progress degree determining function enabled by the dental caries detecting program. More specifically, it is determined whether the sign of ($R_1 - R_2$) is positive (+) (S33), and if the sign is positive (+), a possibility of dental caries is indicated (S34). If the sign is negative (−), it is indicated that the tooth is healthy, and the process returns to S1 in the main processing (S35). Besides this determining method, the correlation between a plurality of luminance data pieces and irradiation intensity values may be obtained, so that if the correlation is "positive," it may be determined that there is dental caries and otherwise it may be determined that the tooth is healthy.

The processing from S33 to S35 is based on the characteristic that the luminance $R_2$ is smaller than the luminance $R_1$ for a dental caries area (a positive correlation with the ultraviolet irradiation intensity), while the luminance $R_2$ is larger than the luminance $R_1$ for a healthy area (a negative correlation with the ultraviolet irradiation intensity), so that the presence/absence of dental caries is determined before the degree of its progress is determined.

The processing after S34 branches to three parts, i.e., processing for a dental caries degree $CD_3$ (branch $D_1$, S41 to S48), processing for a dental caries degree $CD_4$ (branch $D_2$, S51 to S58), and processing for a dental caries degree $CD_5$ (branch $D_3$, S61 to S68) according to the differences in operating processing for the dental caries degrees.

Figure 7:
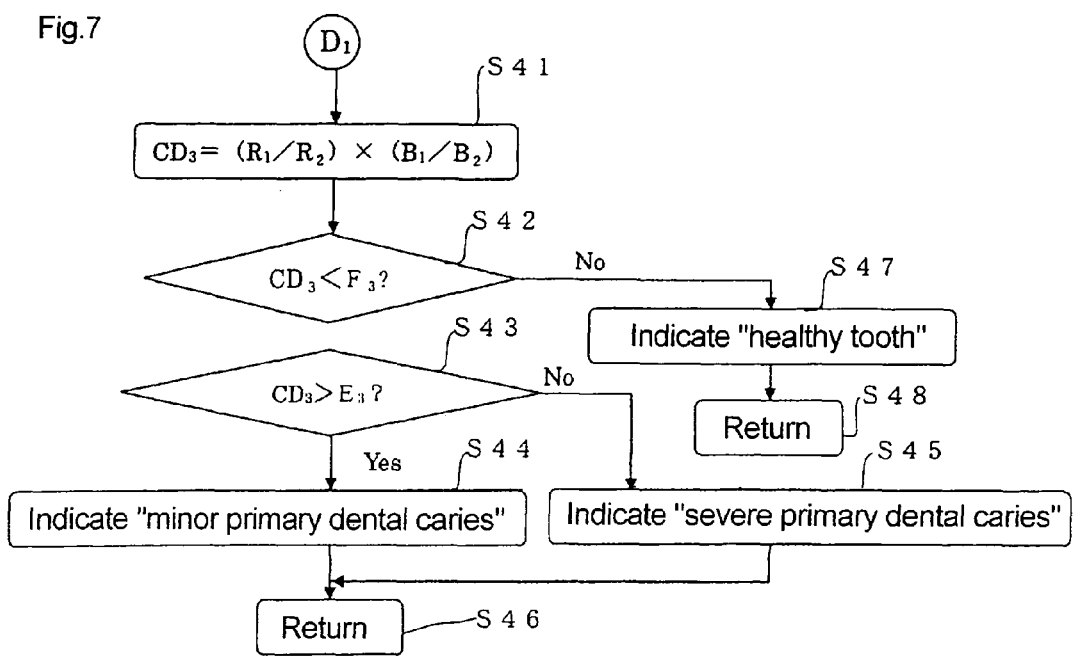
FIG. 7 is a flowchart showing dental caries detecting processing (light intensity change measuring processing, $CD_3$) based on the dental caries detecting program according to the embodiment.

As shown in FIG. 7, in the processing for the dental caries degree $CD_3$, the CPU 15 obtains the luminance values $R_1$, $B_1$ and $G_1$ of the light intensity $U_1$ and the luminance values $R_2$, $B_2$, and $G_2$ of the light intensity $U_2$ according to the dental caries degree operating function enabled by the dental caries detecting program, and using these values, the dental caries degree $CD_3$ is calculated (S41) according to the following formula (3):

$$CD_3 = (R_1/R_2) \times (B_1/B_2) \qquad \text{formula (3)}$$

The dental caries degree $CD_3$ represents dental caries progress degree as a function in consideration of the characteristic that the luminance values $R_2$, $B_2$, and $G_2$ are smaller than $R_1$, $B_1$, and $G_1$, respectively for a dental caries area, while for a healthy area, the luminance values $B_2$ and $G_2$ are smaller than the luminance values $B_1$ and $G_1$, respectively but the luminance value $R_2$ is larger than the luminance value $R_1$.

The processing from S42 to S48 is carried out by the CPU 15 according to the dental caries presence/absence and progress degree determining function enabled by the dental caries detecting program, and is substantially the same as the processing from S23 to S30.

In S42, the dental caries degree $CD_3$ is compared to an upper threshold $F_3$. If the dental caries degree $CD_3$ is equal to or larger than the upper threshold $F_3$, it is indicated that the tooth is healthy, and the process returns to S1 in the main processing (S47 and S48). If the dental caries degree $CD_3$ is smaller than the upper threshold $F_3$, the process proceeds to S43.

In S43, the dental caries degree $CD_3$ is compared to a lower threshold $E_3$. If the dental caries degree $CD_3$ is larger than the lower threshold $E_3$, it is indicated that there is minor primary dental caries (S44). If the dental caries degree $CD_3$ is equal to or smaller than the lower threshold $E_3$, it is indicated that there is severe primary dental caries (S45), and the process returns to S1 in the main processing (S46).

Figure 8:
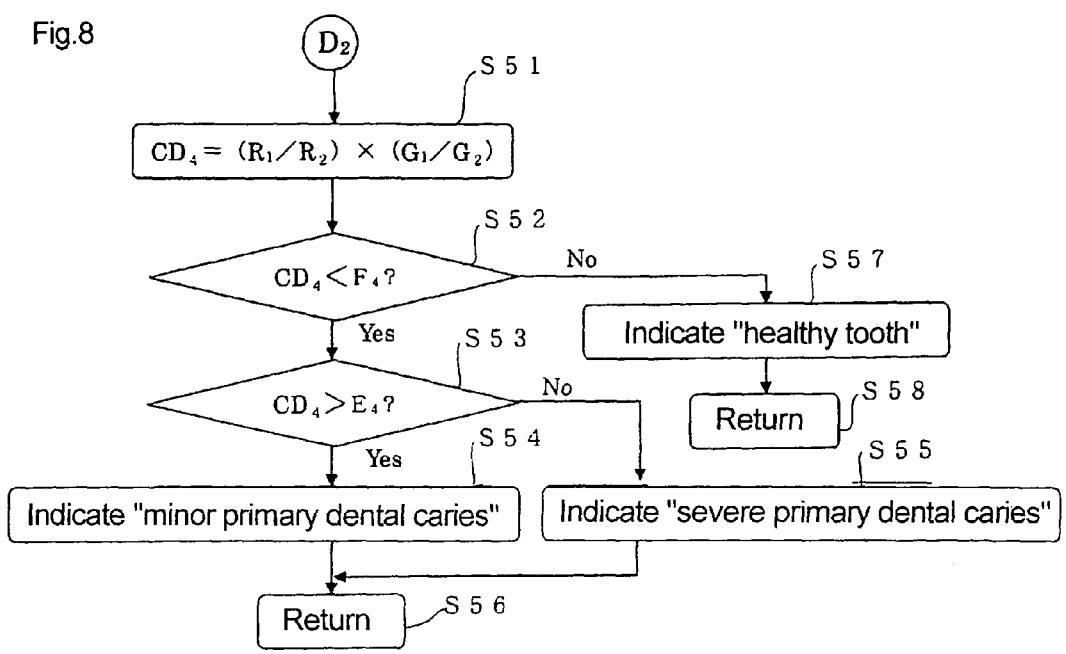
FIG. 8 is a flowchart showing dental caries detecting processing (light intensity change measuring processing, $CD_4$) based on the dental caries detecting program according to the embodiment.

As shown in FIG. 8, the processing for the dental caries degree $CD_4$ is different from the processing for the dental caries degree $CD_3$ only in the processing in S51.

In S51, using the luminance values $R_1$, $B_1$, and $G_1$ of the light intensity $U_1$ and the luminance values $R_2$, $B_2$, and $G_2$ of the light intensity $U_2$, the dental caries degree $CD_4$ is calculated according to the following formula (4):

$$CD_4 = (R_1/R_2) \times (G_1/G_2) \qquad \text{formula (4)}$$

The other processing is carried out in the same manner as that described above, and therefore will not be described.

Figure 9:
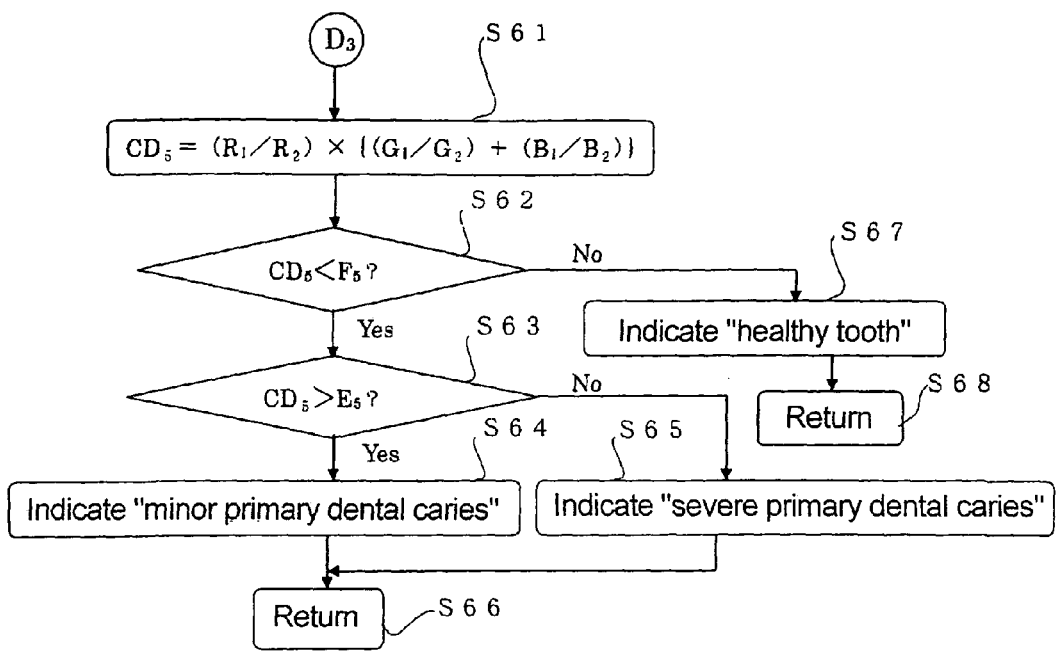
FIG. 9 is a flowchart showing dental caries detecting processing (light intensity change measuring processing, $CD_5$) based on the dental caries detecting program according to the embodiment.

As shown in FIG. 9, the processing for dental caries degree $CD_5$ is different from the processing for the dental caries degree $CD_3$ only in the processing in S61, S62, and S63.

In S61, using the luminance values $R_1$, $B_1$, and $G_1$ of the light intensity $U_1$ and the luminance values $R_2$, $B_2$, and $G_2$ of the light intensity $U_2$, the dental caries degree $CD_5$ is calculated according to the following formula (5):

$$CD_5 = (R_1/R_2) \times \{(B_1/B_2) + (G_1/G_2)\} \qquad \text{formula (5)}$$

In S62, the upper threshold $F_5$ is set in a different manner, and in S63, the lower threshold $E_5$ is set in a different manner. The other processing is carried out in the same manner as that described above, and therefore will not be described.

According to the light intensity change measuring method described above, although not shown, in addition to the dental caries degrees $CD_3$, $CD_4$, and $CD_5$, a dental caries degree $CD_6$ may be calculated according to the following formula (6):

$$CD_6 = (R_1/R_2) \times (B_1/B_2) \times (G_1/G_2) \qquad \text{formula (6)}$$

As in the foregoing, by the dental caries detecting method according to the embodiment, the dental caries degrees CD can be represented by a quantitative function based on the luminance values R, B, and G ranging between high and low energy values. The dental caries degree CD is compared to the lower threshold E and the upper threshold $F_1$ so that it can be determined accurately and with high sensitivity whether primary dental caries not yet fractured by bacteria is actually "healthy tooth," "minor dental caries," or "severe dental caries."

According to the embodiment, the dental caries detecting methods can largely be divided into three measuring kinds, i.e., a method using data obtained from a single location, a method comparing data obtained from two locations, and a measuring method while changing the light intensity. These methods are employed separately or in combination depending upon the purpose or area for measuring, so that the presence/absence and progress degree of dental caries can efficiently and accurately be detected.

More specifically, the method using data from one location can be applied not only to visually observable areas but also areas between teeth or occluded areas that are relatively difficult to obtain an area for comparison. The presence/absence of dental caries or the progress degree of the dental caries can be detected simply by measuring in the single location. The method can advantageously be applied to any area as a method that allows dental caries to be instantaneously detected based on the obtained dental caries degree $CD_1$.

According to the measuring method that compares data from two locations, a visually observable dental caries area or an area suspected to have dental caries is measured in two locations in comparison with a healthy area, so that the presence/absence or degree of progress of the dental caries can be detected. The measuring method is advantageous in that the degree of progress of dental caries can be detected instantaneously based only on the dental caries degree $CD_2$ in consideration of comparison between the dental caries area and the healthy area.

According to the light intensity change measuring method, the same dental caries area is measured at least twice while the intensity of ultraviolet irradiation is changed, and the degree of progress of dental caries can be detected. The measuring method is advantageous in that the presence/absence of dental caries can instantaneously be detected simply by comparing the luminance values $R_1$ and $R_2$ of different light intensities, and that the degree of progress of dental caries corresponding to the depth of the tooth can be obtained in response to changes in the light intensity.

The dental caries detecting method according to the invention can be carried out by using a dental caries detecting system 1 having a dental caries detecting program incorporated therein.

The invention is not limited to the above-described embodiment, and may be modified in various manners.

For example, according to the light intensity measuring method, the light intensity is changed between two levels, but the light intensity may be changed among three or more levels, and arbitrary two kinds of information (fluorescence data) may be obtained to calculate the dental caries degrees $CD_3$ to $CD_6$.

The luminance ratios ($R_1/R_2$) of different light intensities or the like are used for calculating the dental caries degrees $CD_3$ to $CD_6$, while alternatively the luminance inclination or correlation can be used.

The dental caries degree CD may be compared to the lower and upper thresholds E and F, or another different threshold may be added to indicate a moderate degree between the severe and minor degrees. For example, other than the data indicating that the tooth is healthy, the dental caries degree CD itself may be indicated as analysis data at the display 5, and the analysis data may be output to the output device 13.

EXAMPLES

The inventors evaluated the detection accuracy of the dental caries detecting device according to the invention by obtaining the correlation between the method disclosed by Non-patent Document 3 that can measure the degree of dental caries most accurately among state of the art techniques and Examples 1 to 4 and Comparative Examples 1 and 2.

Extracted teeth used for experiments had primary dental caries that could be recovered by non-surgical treatment and had no surface fracture. An experienced dentist visually checked and classified these sample teeth into three kinds, i.e., very primary dental caries (minor), dental caries progressed to some extent (moderate), and dental caries progressed to almost form a cavity (severe).

The classified extracted teeth were measured using the dental caries detecting device according to the invention. Then, according to the method disclosed by Non-patent Document 3, the extracted teeth were sliced into samples for micro X-ray photographing. In Examples, the correlation coefficient was obtained between the results of measuring using the dental caries detecting device according to the invention and the mineral decreasing ratio obtained by the method disclosed by Non-patent Document 3 in order to prove the accuracy of the dental caries detecting device according to the invention.

The mineral decreasing ratio represents the degree of progress of dental caries, and is obtained by analyzing computer images as to an area as deep as 300 microns from the surface using the micro X-ray photographing technique according to the disclosure of Non-patent Document 3. The mineral decreasing ratio in a healthy area is 0%, and when the tooth is entirely fractured and lost, the mineral decreasing ratio is 100%.

The dental caries detecting system 1 according to Examples and a dental caries detecting method using the system will be described. A mercury lamp (Type: CSHG1 manufactured by Nikon Corporation) was used as the ultraviolet irradiation device 2. The mercury lamp was provided with a band-pass filter passing ultraviolet light having a wavelength of not more than 400 nm (Type: E365/10 manufactured by Nikon Corporation) and could efficiently irradiate i ray. The mercury lamp was provided with an ND filter (Type: ND4 manufactured by Nikon Corporation), so that the light intensity can be changed between two levels, $U_1$ (=340 mV/cm$^2$) and $U_2$ (=94 mV/cm$^2$). Ultraviolet light from the mercury lamp was directly irradiated upon a tooth through an optical fiber (made of silica).

A color CCD camera (Type: PDMC IIi manufactured by Polaroid Corporation) was used as the fluorescence receiving device 3. The color CCD was provided with a UV cut filter (Type: BA400 manufactured by Nikon Corporation) passing light of at least 400 nm, so that fluorescence in the visible light range could be image-sensed. The data was A/D-converted to obtain 16-bit luminance values R, B, and G.

A measuring process at different measuring tooth areas with different light intensities $U_1$ and $U_2$ will be described.

As for a dental caries area, three locations, a minor area L, a moderate area M, and a severe area H were measured, and as for a healthy area in the vicinity (in the same tooth), three locations, a healthy area (minor) L', a healthy area (moderate) M', and a healthy area (severe) H' were measured.

Symbols of each of the measuring areas are provided with suffixes "1" and "2" corresponding to the light intensities $U_1$ and $U_2$. For example, "$L_1$" represents a measuring area for a minor dental caries area irradiated with ultraviolet light of the light intensity $U_1$, while "$H_{2,1}$" is the measuring location of a severe dental caries area irradiated with ultraviolet light of the light intensities $U_1$ and $U_2$.

The relation between the light intensities $U_1$ and $U_2$ for each of the measuring areas and the luminance values R, B, and G measured according to Examples is shown in FIG. 10, and data about the light intensities $U_1$ and $U_2$ and the luminance values R, B, and G ($2^{16}$=65536 in maximum) is given in Tables 1 to 3.

TABLE 1

| measuring area | | luminance R | luminance G | luminance B |
|---|---|---|---|---|
| $L_1'$ | Healthy_340 mV/cm² | 2965 | 36420 | 64597 |
| $L_2'$ | Healthy_94 mV/cm² | 3408 | 13465 | 34529 |
| $L_1$ | Minor_340 mV/cm² | 6345 | 23169 | 46429 |
| $L_2$ | Minor_94 mV/cm² | 4860 | 7892 | 16608 |

TABLE 2

| measuring area | | luminance R | luminance G | luminance B |
|---|---|---|---|---|
| $M_1'$ | Healthy_340 mV/cm² | 871 | 31447 | 61884 |
| $M_2'$ | Healthy_94 mV/cm² | 3561 | 12121 | 30485 |
| $M_1$ | Minor_340 mV/cm² | 9039 | 28355 | 51510 |
| $M_2$ | Minor_94 mV/cm² | 6432 | 11072 | 20589 |

TABLE 3

| measuring area | | luminance R | luminance G | luminance B |
|---|---|---|---|---|
| $H_1'$ | Healthy_340 mV/cm² | 284 | 40539 | 65279 |
| $H_2'$ | Healthy_94 mV/cm² | 2797 | 16054 | 41853 |
| $H_1$ | Minor_340 mV/cm² | 7571 | 16315 | 28406 |
| $H_2$ | Minor_94 mV/cm² | 6525 | 7385 | 11810 |

Example 1

In Example 1, according to the "measuring method using data obtained from a single location" in the dental caries detecting method according to the embodiment, the dental caries degree $CD_1$ was calculated for the measuring areas $L_1$, $M_1$, $H_1$, $L_1'$, $M_1'$, and $H_1'$ of the light intensity $U_1$, and the correlation coefficients between the dental caries degree $CD_1$ and the mineral decreasing ratio were obtained.

Comparative Example 1

In Comparative Example 1, according to the technique disclosed by Patent Document 2, the light intensity of the ultraviolet irradiation is set to $U_1$, and measuring was carried out for the measuring areas $L_1$, $M_1$, $H_1$, $L_1'$, $M_1'$, and $H_1'$. The color CCD was provided with a cut filter passing light of at least 620 nm, so that the color CCD could obtain only an image of red fluorescence. The image was converted into a gray image, and the red luminance (16 bit) for each of the measuring areas was obtained. The correlation coefficients between the red luminance values and the mineral decreasing ratios were obtained. The results of measurement according to Example 1 and Comparative Example 1 are given in Table 4.

TABLE 4

| measuring area | | mineral decreasing ratio (%) | Example 1 (absolute value) dental caries degree $CD_1$ | Comparative Example 1 red luminance |
|---|---|---|---|---|
| $L_1$ | Dental caries area (minor) | 11.2 | 0.137 | 6345 |
| $M_1$ | Dental caries area (moderate) | 25.6 | 0.166 | 9039 |
| $H_1$ | Dental caries area (severe) | 68.9 | 0.267 | 7571 |
| $L_1'$ | Healthy area | 0 | 0.046 | 2965 |
| $M_1'$ | Healthy area | 0 | 0.014 | 871 |
| $H_1'$ | Healthy area | 0 | 0.004 | 284 |
| correlation coefficient with mineral decreasing ratio | | | 0.934 | 0.702 |

As shown in Table 4, a high mineral decreasing ratio indicates that the dental caries is much in progress. It is established that the correlation between the dental caries degree $CD_1$ and the mineral decreasing ratio is high in Example 1, so that the dental caries degree $CD_1$ may represent the degree of progress of dental caries as an objective and quantitative value.

In order to accurately obtain the progress degree of dental caries, the red luminance must be increased as a value of the mineral decreasing ratio. In contrast, in Comparative Example 1, the luminance levels are reversed between the moderate dental caries area $M_1$ and the severe dental caries area $H_1$, which is not necessarily in coincidence with the degree of progress of the dental caries, and therefore it is difficult to detect the degree of progress of the dental caries.

Example 2

In Example 2, according to the "comparison measuring method" among the dental caries detecting methods according to the embodiment, the dental caries degree $CD_2$ was calculated for the measuring areas ($L_1$, $L_1'$), ($M_1$, $M_1'$), and ($H_1$, $H_1'$) of the light intensity $U_1$ and the correlation coefficients between the calculated dental caries degrees $CD_2$ and the mineral decreasing ratios were obtained.

Comparative Example 2

In Comparative Example 2, according to the conventional technique disclosed by Patent Document 1, the light intensity of ultraviolet light was set to $U_1$, and measuring is carried out for the measuring areas ($L_1$, $L_1'$), ($M_1$, $M_1'$), and ($H_1$, $H_1'$). The color CCD was provided with a cut filter passing light of at least 520 nm, so that an image of single color light from 520 nm to 800 nm can be obtained. The image was converted into a gray image, the luminance of the dental caries area (16 bits) and the luminance of the healthy area (16 bits) were obtained for each of the measuring areas, and the ratio was calculated as relative luminance. The correlation coefficients between the relative luminance values and the mineral decreasing ratios were obtained.

The results of measurement according to Example 2 and Comparative Example 2 are given in Table 5.

TABLE 5

|  |  | mineral decreasing ratio (%) | Example 2 (relative comparison) dental caries degree $CD_2$ | Comparative Example 2 relative luminance |
|---|---|---|---|---|
| $L_1, L_1'$ | Minor area | 11.2 | 6.14E+07 | 0.730 |
| $M_1, M_1'$ | Moderate area | 25.6 | 8.47E+07 | 0.944 |
| $H_1, H_1'$ | Severe area | 68.9 | 2.69E+08 | 0.493 |
| correlation coefficient with mineral decreasing ratio |  |  | 0.990 | −0.742 |

As in Table 5, it is established that the correlation coefficient between the dental caries degree $CD_2$ and the mineral decreasing ratio is high and the dental caries degree $CD_2$ can represent the degree of progress of dental caries by an objective quantitative value. Meanwhile, the relative luminance levels are reversed between the moderate areas of dental caries ($M_1$, $M_1'$) and the severe areas of dental caries ($H_1$, $H_1'$), and therefore only the luminance of single color light does not necessarily match the degree of progress of the dental caries. It is therefore difficult to detect the degree of progress of dental caries.

Example 3

In Example 3, according to the "light intensity change measuring method" among the dental caries detecting methods according to the embodiment, luminance changes ($R_1-R_2$), ($G_1-G_2$), and ($B_1-B_2$) and the dental caries degrees $CD_3$ and $CD_4$ were calculated for the measuring areas $L_{2,1}$, $M_{2,1}$, $H_{2,1}$, $L_{2,1}'$, $M_{2,1}'$, and $H_{2,1}'$ of the light intensities $U_1$ and $U_2$, and the correlation coefficients between the dental caries degrees $CD_3$ and $CD_4$ and the mineral decreasing ratios were obtained. The results of measuring according to Example 3 are given in Tables 6 and 7.

TABLE 6

| measuring area |  | mineral decreasing ratio (%) | luminance change (340-94) | | |
|---|---|---|---|---|---|
|  |  |  | $R_1-R_2$ | $G_1-G_2$ | $B_1-B_2$ |
| $L_{2,1}$ | Dental caries area (minor) | 11.2 | 1485 | 15277 | 27821 |
| $M_{2,1}$ | Dental caries area (moderate) | 25.6 | 2607 | 17283 | 30921 |
| $H_{2,1}$ | Dental caries area (severe) | 68.9 | 1046 | 8931 | 16596 |
| $L_{2,1}'$ | Healthy area | 0 | −443 | 22955 | 30068 |
| $M_{2,1}'$ | Healthy area | 0 | −2690 | 19326 | 31399 |
| $H_{2,1}'$ | Healthy area | 0 | −2514 | 24485 | 23426 |
| correlation coefficient with mineral decreasing ratio |  |  | 0.557 | −0.890 | −0.739 |

TABLE 7

|  |  | Example 3 (intensity change) | | |
|---|---|---|---|---|
| measuring area |  | mineral decreasing ratio (%) | dental caries degree $CD_3$ | Dental caries degree $CD_4$ |
| $L_{2,1}$ | minor area | 11.2 | 3.649 | 3.833 |
| $M_{2,1}$ | Moderate area | 25.6 | 3.516 | 3.599 |
| $H_{2,1}$ | Severe area | 68.9 | 2.791 | 2.564 |
| correlation coefficient with mineral decreasing ratio |  |  | −0.995 | −0.998 |

As can be seen from Table 6, the sign of the luminance change ($R_1-R_2$) is an objective criterion for determining the presence/absence of dental caries. It is also established from Table 7 that the correlation coefficients between the dental caries degrees $CD_3$ and $CD_4$ and the mineral decreasing ratios are high, so that the dental caries degrees $CD_3$ and $CD_4$ can represent the degrees of progress of dental caries by objective quantitative values.

Example 4

In Example 4, dental caries degrees $CD_5$ and $CD_6$ were calculated in the same manner as in Example 3, and the correlation coefficients between the dental caries degrees $CD_5$ and $CD_6$ and the mineral decreasing ratios were obtained.

While the dental caries degrees $CD_3$ and $CD_4$ are calculated based on the luminance value R and one of the luminance values B and G, the dental caries degrees $CD_5$ and $CD_6$ are calculated based on the luminance values R, B, and G. The results of measuring according to Example 4 are given in Table 8.

TABLE 8

|  |  | mineral decreasing ratio (%) | Example 4 (intensity change) | |
|---|---|---|---|---|
| measuring area |  |  | dental caries degree $CD_5$ | dental caries degree $CD_6$ |
| $L_{2,1}$ | Minor area | 11.2 | 7.48 | 10.71 |
| $M_{2,1}$ | Moderate area | 25.6 | 7.11 | 9.00 |
| $H_{2,1}$ | Severe area | 68.9 | 5.35 | 6.17 |
| correlation coefficient with mineral decreasing ratio |  |  | −0.997 | −0.990 |

It is established from Table 8 that the correlation coefficients between the dental caries degrees $CD_5$ and $CD_6$ and the mineral decreasing ratios are high, and the dental caries degrees $CD_5$ and $CD_6$ can represent the degree of progress of dental caries by objective quantitative values.

According to the invention, dental caries detecting device and method that allow primary dental caries to be accurately detected with high sensitivity and the progress degree of the dental caries to be detected can be provided.

INDUSTRIAL APPLICABILITY

The invention is applicable to a technique of detecting the presence/absence of primary dental caries and the degree of progress of the primary dental caries in the field of non-destructively detecting primary dental caries.

The invention claimed is:
1. A dental caries detecting device, comprising:
an ultraviolet light source that irradiates ultraviolet light of at least two different intensities, including ultraviolet light of first intensity and ultraviolet light of second intensity, onto a single measuring area of a tooth;

a fluorescence receiving portion that receives fluorescence from the single measuring area of the tooth in response to the ultraviolet irradiation of the at least two different light intensities from the ultraviolet light source;

a fluorescence data analysis portion that analyzes fluorescence data transmitted from the fluorescence receiving portion; and a data display portion that displays data analyzed by the fluorescence data analysis portion, wherein the fluorescence receiving portion receives first fluorescence by the ultraviolet light of first intensity and transmits first fluorescence data to the fluorescence data analysis portion, the fluorescence receiving portion receives second fluorescence by the ultraviolet light of second intensity and transmits second fluorescence data to the fluorescence data analysis portion, and said fluorescence data analysis portion analyzes the first fluorescence data and the second fluorescence data in at least one wavelength band for detection of a dental caries.

2. The dental caries detecting device according to claim 1, wherein said fluorescence data analysis portion calculates a degree of progress of dental caries based on said fluorescence intensity in a first wavelength band selected in a wavelength band from 550 nm to 810 nm and having a wavelength width from 0.1 nm to 260 nm, and said fluorescence intensity in a second wavelength band selected from a wavelength band from 380 nm to 550 nm and having a wavelength width from 0.1 nm to 170 nm.

3. The dental caries detecting device according to claim 1, wherein said fluorescence data analysis portion calculates a degree of progress of dental caries based on said fluorescence intensity in a first wavelength band selected from a wavelength band from 550 nm to 810 nm and having a wavelength width from 0.1 nm to 260 nm, and one or more of said fluorescence intensity in a second wavelength band selected from a wavelength band from 380 nm to 550 nm and having a wavelength width from 0.1 nm to 170 nm and said fluorescence intensity in a third wavelength band selected from a wavelength band from 450 nm to 650 nm and having a wavelength width from 0.1 nm to 200 nm.

4. The dental caries detecting device according to claim 3, wherein said fluorescence receiving portion comprises an optical device that can extract information related to said fluorescence intensity in said first wavelength band and said second and/or third wavelength band from a visible light range.

5. The dental caries detecting device according to claim 4, wherein said optical device is one of a spectroscopic luminance meter, a color CCD, a CMOS, or an optical sensor with a color filter for at least two colors.

6. The dental caries detecting device according to claim 5, wherein an output intensity of said ultraviolet light source is adjustable.

7. The dental caries detecting device according to claim 6, wherein said ultraviolet light source is an ultraviolet LED.

8. The dental caries detecting device according to claim 1, wherein the fluorescence receiving portion includes a UV cut filter configured to pass light of at least 400 nm.

9. A dental caries detecting method, comprising:
irradiating a single measuring area of a tooth with ultraviolet light of at least two different intensities from a light source;

obtaining fluorescence from said single measuring area for the at least two different light intensities of the ultraviolet light from the light source among light intensities $U_1$, $U_2$, ..., and $U_n$ where $U_1 > U_2 ... > U_n$ as first, second, ..., and n-th information, respectively;

obtaining first fluorescence intensities $R_1$, $B_1$, and $G_1$, second fluorescence intensities $R_2$, $B_2$, and $G_2$, ..., and n-th fluorescence intensities $R_n$, $B_n$, and $G_n$ of said fluorescence in at least two wavelength bands selected from a first wavelength band selected from a wavelength band from 550 nm to 810 nm and having a wavelength from 10 nm to 260 nm, a second wavelength band selected from a wavelength band from 380 nm to 550 nm and having a wavelength width from 10 nm to 170 nm, and a third wavelength band selected from a wavelength band from 450 nm to 650 nm and having a wavelength width from 10 nm to 200 nm based on said first information, the second information, ..., and the n-th information;

carrying out calculation according to the following formula (5):

$$(R_1-R_2)+(R_2-R_3)+ \ldots +(R_{n-1}-R_n) \quad \text{formula (5)}$$

and determining that there is a possibility of dental caries if a sign of a result obtained from formula (5) is positive, and determining that the tooth is healthy if the sign is negative or a result is zero.

10. The dental caries detecting method according to claim 9, further including:
calculating a dental caries degree $CD_3$ according to the following formula (6) if it is determined that there is a possibility of dental caries, $$CD_3 = (R_{n-1}/R_n) \times (B_{n-1}/B_n) \quad \text{formula (6)}$$

comparing a value of said dental caries degree $CD_3$ and an upper threshold $F_3$;

determining the tooth as being healthy if the value of said dental caries degree $CD_3$ is equal to or larger than said upper threshold $F_3$ and determining the presence of dental caries if the value of said dental caries degree $CD_3$ is smaller than said upper threshold $F_3$.

11. The dental caries detecting method according to claim 10, further including:
comparing the value of said dental caries degree $CD_3$ and a lower threshold $E_3$ if the presence of dental caries is determined; and determining that the dental caries is minor if the value of said dental caries degree $CD_3$ is equal to or larger than said lower threshold $E_3$, and determining that the dental caries is severe if the value of said dental caries degree $CD_3$ is smaller than said lower threshold $E_3$.

12. The dental caries detecting method according to claim 9, further including:
calculating a dental caries degree $CD_4$ according to the following formula (7) if it is determined that there is a possibility of dental caries, $$CD_4 = (R_{n-1}/R_n) \times (G_{n-1}/G_n) \quad \text{formula (7)}$$

comparing a value of said dental caries degree $CD_4$ and an upper threshold $F_4$; and determining the tooth as being healthy if the value of said dental caries degree $CD_4$ is equal to or larger than said upper threshold $F_4$, and determining the presence of dental caries if the value of said dental caries degree $CD_4$ is smaller than said upper threshold $F_4$.

13. The dental caries detecting method according to claim 12, further including:
comparing the value of said dental caries degree $CD_4$ and a lower threshold $E_4$ if the presence of dental caries is determined; and
determining that the dental caries is minor if the value of said dental caries degree $CD_4$ is equal to or larger than said lower threshold $E_4$ and determining that the dental caries is severe if the value of said dental caries degree $CD_4$ is smaller than said lower threshold $E_4$.

14. The dental caries detecting method according to claim 9, further including:
calculating a dental caries degree $CD_4$ according to the following formula (8) if it is determined that there is a possibility of dental caries, $$CD_5 = (R_{n-1}/R_n) \times \{(G_{n-1}/G_n) + (B_{n-1})\} \quad \text{formula (8)}$$

comparing a value of said dental caries degree $CD_5$ and an upper threshold $F_5$; and
determining the tooth as being healthy if the value of said dental caries degree $CD_5$ is equal to or larger than said upper threshold $F_5$, and determining the presence of dental caries if the value of said dental caries degree $CD_5$ is smaller than said upper threshold $F_5$.

15. The dental caries detecting method according to claim 14, further including:
comparing the value of said dental caries $CD_5$ and a lower threshold $E_5$ if the presence of dental caries is determined; and
determining that the dental caries is minor if the value of said dental caries $CD_5$ is equal to or larger than the lower threshold $E_5$ and determining that the dental caries is severe if the value of said dental caries degree $CD_5$ is smaller than said lower threshold $E_5$.

16. The dental caries detecting method according to any one of claims 9 to 15, wherein said n is 2.

17. A dental caries detecting computer readable medium including computer executable instructions, wherein the instructions, when executed by a processor, cause the processor to perform the dental caries detecting method according to any one of claims 9 to 15.

18. The dental caries detecting method according to claim 9, wherein the obtaining the fluorescence includes utilizing a UV cut filter to pass light of at least 400 nm.

19. A dental caries detecting method that detects dental caries based on fluorescence from a measuring area of a tooth, comprising:
irradiating the measuring area with ultraviolet light of at least two different light intensities from a light source;
obtaining fluorescence from said measuring area as first information, second information, .., and n-th information for at least two different light intensities of the ultraviolet light from the light source $U_1, U_2, \ldots,$ and $U_n$ where $U_1 > U_2 \ldots > U_n$;
obtaining a first fluorescence intensity $R_1$, a second fluorescence intensity $R_2, \ldots,$ and an n-th fluorescence intensity $R_n$ in a first wavelength band selected from a wavelength band from 550 nm to 810 nm and having a wavelength width from 10 nm to 260 nm based on said first information, the second information, . . . , and the n-th information;
calculating according to the following formula (5):

$$(R_1-R_2)+(R_2-R_3)+\ldots+(R_{n-1}-R_n) \quad \text{formula (5)}$$

and
determining that there is a possibility of dental caries if a sign of a result obtained from formula (5) is positive, and determining that the tooth is healthy if the sign is negative or the result is zero.

20. The dental caries detecting method according to claim 19, wherein the obtaining the fluorescence includes utilizing a UV cut filter to pass light of at least 400 nm.

* * * * *

UNITED STATES PATENT AND TRADEMARK OFFICE
CERTIFICATE OF CORRECTION

| | |
|---|---|
| PATENT NO. | : 7,955,076 B2 |
| APPLICATION NO. | : 10/551842 |
| DATED | : June 7, 2011 |
| INVENTOR(S) | : Atsushi Yamagishi |

It is certified that error appears in the above-identified patent and that said Letters Patent is hereby corrected as shown below:

On the title page, Item (86), the Application Filing Date is incorrect. Item (86) should read:

-- (86) PCT No.: PCT/JP2004/004861

§ 371 (c)(1),
(2), (4) Date: Nov. 15, 2006 --

Signed and Sealed this
Ninth Day of August, 2011

David J. Kappos
*Director of the United States Patent and Trademark Office*